US00PP10990P

United States Patent [19]

Evison et al.

[11] Patent Number: Plant 10,990

[45] Date of Patent: Jul. 6, 1999

[54] CLEMATIS PLANT NAMED 'POULALA'

[76] Inventors: Raymond J. Evison, Domarie Vineries, Les Sauvagnees, St. Sampsons, Guernsey, Channel Islands, United Kingdom, GY2 4AF; Mogens N. Olesen, Poulsen Roser International, S.A.R.L., Broze, F-81600 Gaillac, France

[21] Appl. No.: 08/926,876

[22] Filed: Sep. 10, 1997

[51] Int. Cl.[6] ..... A01H 5/00

[52] U.S. Cl. ..... Plt./228

[58] Field of Search ..... Plt./54.1, 228

[56] References Cited

PUBLICATIONS

UPOV CD–ROM. Clematis named 'Poulala', Plant Breeder Rights 97–1107, Canada, 1997.

*Primary Examiner*—Howard J. Locker
*Assistant Examiner*—Melissa L. Kimball

[57] ABSTRACT

A new Clematis cultivar which produces creamy white, almost yellow, fully formed and round flowers. The variety is climbing and clinging and suitable for patio container growth. The variety successfully propagates from softwood cuttings and is suitable for ornamental use in outdoor settings in a variety of climatic conditions. This new and distinct variety has shown to be uniform and stable in the resulting generations from asexual propagation.

2 Drawing Sheets

SUMMARY OF THE INVENTION

The present invention constitutes a new and distinct variety of Clematis which originated from a controlled crossing between the unpatented Clematis variety 'Marie Boisselot' and a plant of the collected species *Clematis henryi* in a cultivated area. The two unpatented parents were crossed and the resulting seed was planted in a controlled environment. The new variety is named 'POULala'.

The objective of the hybridization of this Clematis variety for commercial glasshouse and nursery culture was to create a new and distinct variety with unique characteristics, such as:

1. Creamy white flowers (near yellow).
2. Improved repeat flowering over the nearest variety 'Moonlight', an unpatented variety of *C. patens*.
3. Attractive foliage with broad leaflets.
4. Plant growth more vigorous than other varieties in the Cream/Yellow Color Group.

These qualities were not previously known in combination in commercially available Clematis cultivars of this type and distinguish 'POULala' from all other varieties of which we are aware.

The seeds from the hybridization were germinated and evaluations were conducted of the resulting Clematis plants in a controlled environment. 'POULala' was selected by the inventors as a single plant from the progeny of the aforementioned hybridization.

'POULala' was selected by Raymond J. Evison and Mogens N. Olesen in their Clematis development program in Fredensborg, Denmark in May 1989.

Asexual reproduction of 'POULala' by cuttings was first done by Raymond J. Evison and Mogens N. Olesen in Domarie Vineries Les Sauvagees, St. Sampsons, Guernsey, Channel Islands, United Kingdom in May 1989 and subsequent propagations have demonstrated that the characteristics of 'POULala' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers and leaves of the new variety, with different flowers shown in various stages of maturity. The flower form, tepal counts, flower colors, flower buds, floral parts, and the cultivar's foliage are depicted.

Specifically illustrated in Sheet 1:

1. Stem showing branching and the attachment of the floral parts;
2. leaves and leaflets;
3. front and rear view of a complete flower;
4. detached tepals;
5. flower buds prior to opening;
6. floral parts.

Specifically illustrated in Sheet 2 is a blooming plant growing in an outdoor environment.

DETAILED DESCRIPTION OF THE VARIETY

The following is a detailed description of 'POULala' as observed in its growth throughout the flowering period in glasshouses at Domarie Vineries Les Sauvagees, St. Sampsons, Guernsey, Channel Islands, United Kingdom. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing commercially cultivated variety is Clematis 'Moonlight'. Chart 1 details several physical characteristics of 'POULala' and the comparison variety.

Chart 1

| | 'POULala' | 'Moonlight' |
|---|---|---|
| Typical leaf width (mature leaf of present seasons growth) | 45 mm | 30 mm |
| Spring flowering | yes | yes |
| Repeat flowering between spring - autumn | occasionally | none |
| Autumn flowering | yes | very rarely |
| Vigor | moderately vigorous | poor vigor |
| Flower tepal overlap | strong overlap giving flower round appearance | slight overlap giving 'star' appearance |

Parents: Clematis 'Marie Boisselot'×*Clematis henryi.*
Classification:
*Botanical.*—*Clematis L.*
*Commercial.*—Early large-flowered cultivar.

FLOWER AND FLOWER BUD

Blooming habit: Spring, Fall.
Flower bud:
*Size.*—40–60 mm in length.
*Bud form.*—Pointed ovoid.
*Bud color.*—Grayish green at ¼ opening.
*Tepals.*—Color is R.H.S. 10 D of the Yellow Color Group.
*Peduncle.*—Surface: Smooth. Length: 80–120 mm average length. Color: Medium green. R.H.S. 137 B of the Green Group. Strength: Erect
*Borne.*—Singly.
Flower bloom:
*Size.*—Medium. 130 mm. diameter on average.
*Form.*—Upon opening, convex. Completely open, flat.
*Color.*—Upon opening, the upper surface is R.H.S. 10 D of the Yellow Color Group. After opening, the upper surface is R.H.S. 10 D of the Yellow Color Group. After opening, the reverse surface is R.H.S. 10 D of the Yellow Color Group. The base of the tepal is greenish in color. The general tonality from a distance is Creamy White.
*Variations.*—None.
*Fragrance.*—None.
*Lasting quality on plant and as a cut flower.*—On the plant, flowers last 2–3 weeks. As a cut flower, 3–4 days.
Tepals:
*Petalage.*—Single. Average range: 6–8.
*Shape.*—Individual tepal shape is rounded-elliptic.
*Cross section.*—Slightly reflexed.
*Undulation of margin.*—Medium.
*Tepal apex.*—Broadly acute.
*Recurvature of tip.*—Slightly curved.
*Persistence.*—Drop off cleanly.
*Arrangement.*—Tepals are arranged regularly.
Reproductive organs:
*Pollen.*—Yellow white.
*Anthers.*—Size: Medium. Color: Light Yellow. Arrangement: Regular.
*Filaments.*—Color: White.
*Fruit.*—Occasional seed set, with seed ripening in August-September. Diameter 7 mm. Yellow-Green Group 148A turning Brown Group 200D. Duration on plant until mid winter.

PLANT

Plant form: Climbing, spreading.
Plant growth: Moderately vigorous.
Height: Seasons growth attains 2.5–3 meters.
Hardiness: Trials to date show the variety hardy in USDA Zones 4–9.
Stems:
*Color.*—Young wood: Green Group 138B. Older wood: Brown Group 200D.
*Internodes.*—Cylindrical. Length 150 mm.
*Petioles.*—Incidence: Moderate. Size: Average length: 60 mm. Color: Brown. Clasping: Clasps by leaf petiole.
*Bark.*—Young wood: Smooth. Older wood: Rough.
Plant foliage: Deciduous. Leaves are trifoliate.
*Leaf size.*—Medium. Length: 60 mm.
*Abundance.*—Average.
*Color.*—Top: Medium green. R.H.S. 137 B of the Green Color Group. Bottom: Light green. R.H.S. 137 C the Green Color Group. New growth: Green. Older growth: Medium green.
Plant leaves and leaflets:
*Stipules.*—Absent.
*Petiole.*—Length: 50 mm. Underneath: Without prickles.
*Leaf edge.*—Terminal leaflet margin is entire.
*Shape.*—Base of leaflet: Rounded. Apex of leaflet: Acute.
*Texture.*—Average thickness. Upper side: Glabrous. Lower side: Ribbed.
*Surface.*—Matte Finish.
Disease resistance: The cultivar is subject to those diseases that normally attack Clematis, however the variety is more tolerant to mildew than most Clematis.

We claim:

1. A new and distinct variety of Clematis plant, substantially as herein illustrated and described, as a distinct and novel Clematis variety due to its abundant creamy white flowers, improved repeat flowering, attractive foliage, and vigorous growth; which make the variety suitable for use in the nursery industry.

* * * * *

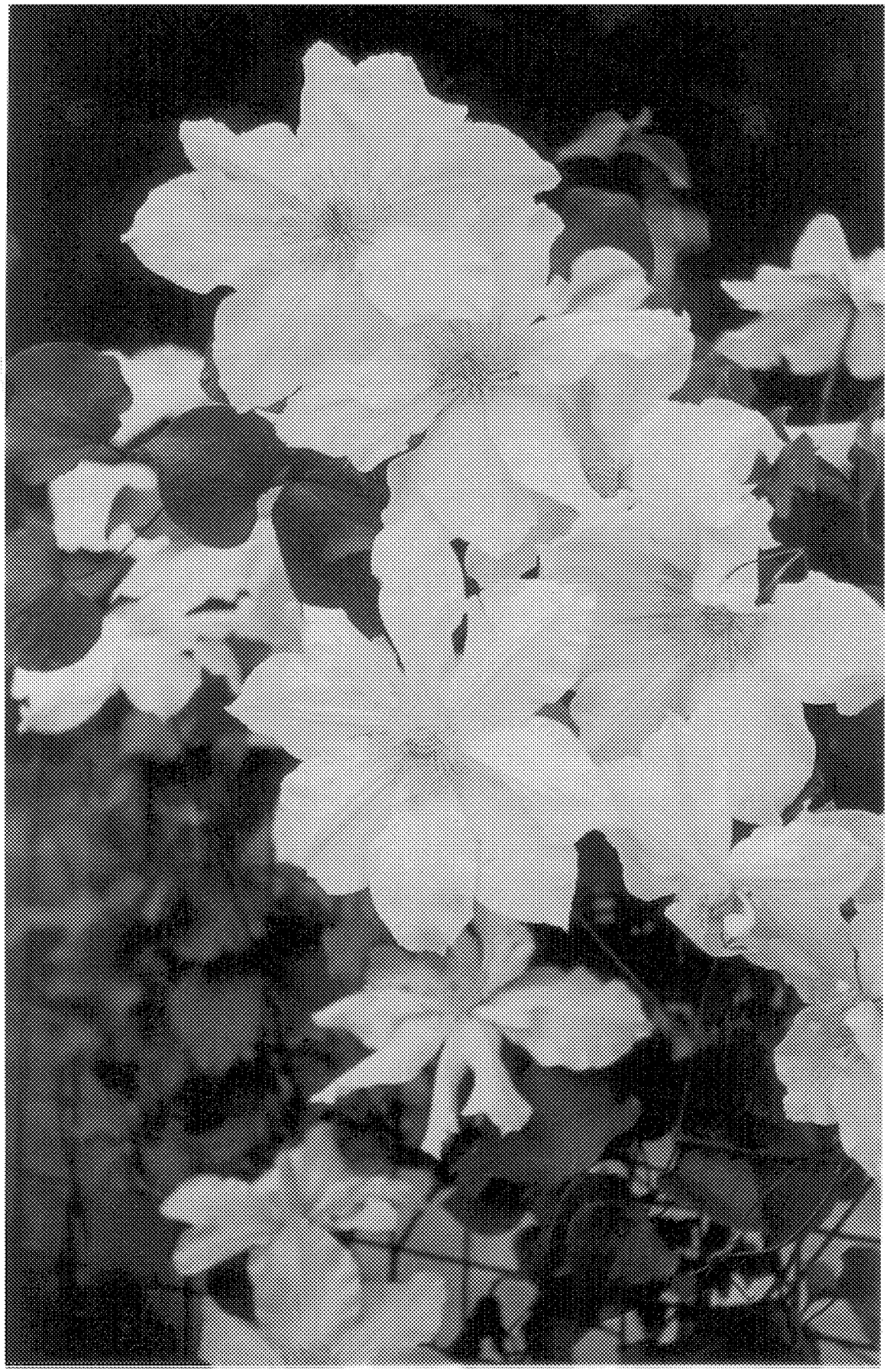

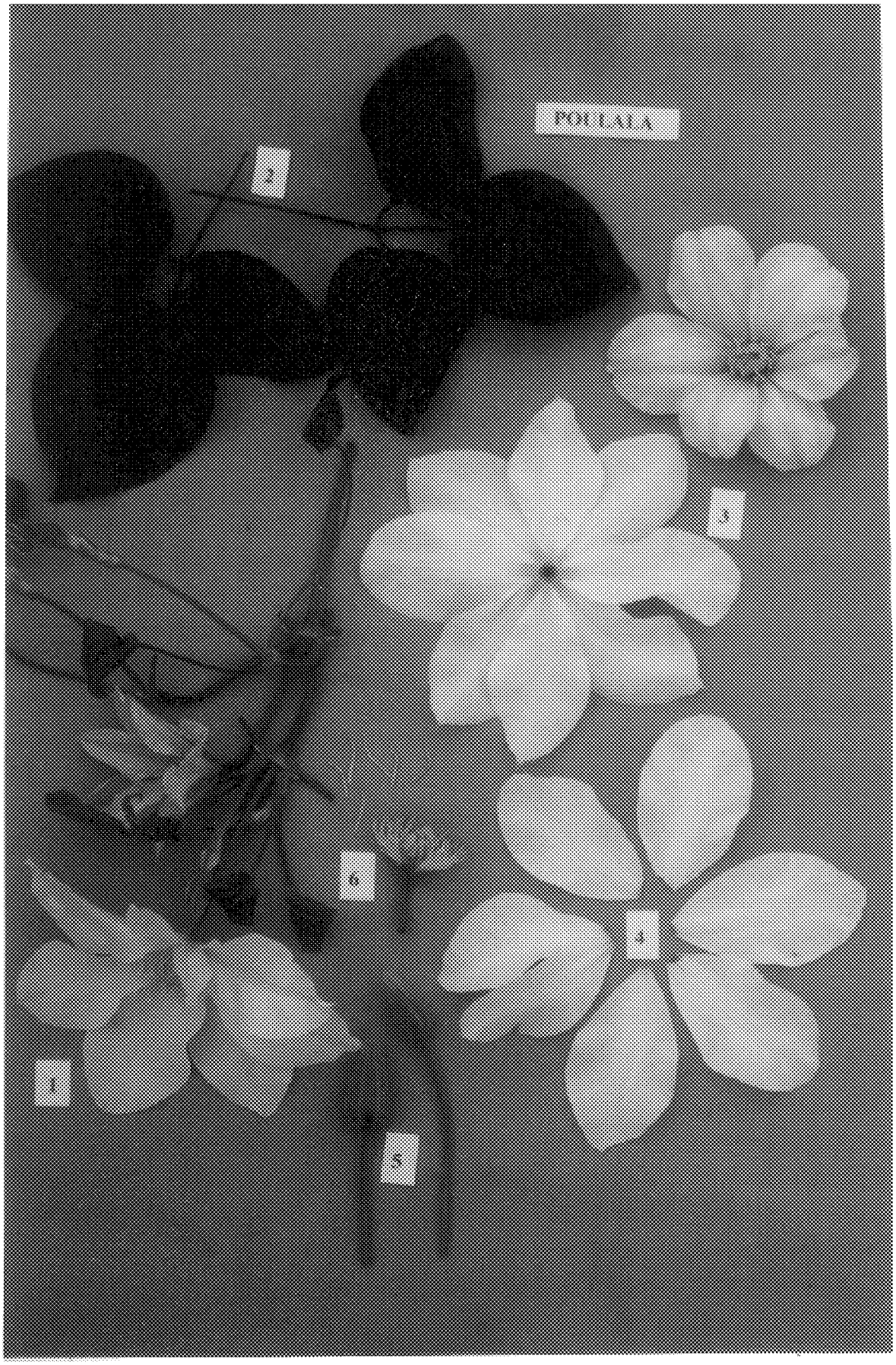
POLLALA
2
3
6
4
1
5